United States Patent [19]

Karthaus et al.

[11] Patent Number: 5,472,667
[45] Date of Patent: Dec. 5, 1995

[54] METHOD AND APPARATUS FOR RECOVERING A STERILIZING GAS

[75] Inventors: Michael Karthaus, Neuss; Olaf Babel, Hattingen; Peter Hermanns, Wesel; Klaus Hermanns, Hünxe; Gerhard Kusenberg, Wesel; Norbert Hagenbruck, Oberhausen, all of Germany

[73] Assignees: Air Products GmbH Werk Hattigen; Herco Kühltechnik Hermanns und Co. GmbH, both of Germany

[21] Appl. No.: 301,309

[22] Filed: Sep. 6, 1994

Related U.S. Application Data

[63] Continuation of Ser. No. 882,486, May 13, 1992, abandoned.

[30] Foreign Application Priority Data

May 27, 1991 [DE] Germany ............... 41 17 306.6

[51] Int. Cl.[6] ............................................. A61L 9/00
[52] U.S. Cl. ......................................... 422/31; 422/34
[58] Field of Search .......................... 422/30, 31, 33, 422/34, 292, 295; 95/95

[56] References Cited

U.S. PATENT DOCUMENTS

| 3,372,980 | 3/1968 | Satas ............................. 422/34 |
| 3,549,312 | 12/1970 | Ernst ............................. 422/31 |
| 3,850,592 | 11/1974 | Huffman ......................... 95/123 |
| 3,989,461 | 11/1976 | Skocypec et al. .............. 422/111 |
| 4,203,943 | 5/1980 | Gillis et al. .................... 422/33 |
| 4,241,010 | 12/1980 | Baran ............................. 422/33 |
| 4,430,306 | 2/1984 | Namba et al. .................. 422/31 |
| 4,764,351 | 8/1988 | Hennebert et al. ............. 422/33 |
| 4,770,851 | 9/1988 | Joslyn ............................. 422/34 |
| 4,812,292 | 3/1989 | Joslyn ............................. 422/31 |
| 4,822,563 | 4/1989 | Joslyn ............................. 422/31 |
| 4,874,580 | 10/1989 | Sugisawa et al. .............. 422/26 |
| 4,954,315 | 9/1990 | Brahmbhatt .................... 422/31 |
| 4,971,761 | 11/1990 | Johnson ......................... 422/34 |
| 5,128,101 | 7/1992 | Boynton ......................... 422/31 |

FOREIGN PATENT DOCUMENTS

| 0130319 | 5/1984 | European Pat. Off. . |
| 0326985 | 1/1989 | European Pat. Off. . |
| 2313484 | 10/1974 | Germany ....................... 422/31 |
| 2745961 | 4/1979 | Germany ....................... 422/31 |
| 564646 | 10/1944 | United Kingdom . |

OTHER PUBLICATIONS

Kirk–Othmer, "Ethylene Oxide", *Encyclopedia of Chemical Technology*, 3rd Edition, vol. 9, pp. 461–464 (1980).

*Primary Examiner*—Robert J. Warden
*Assistant Examiner*—Robert Carpenter
*Attorney, Agent, or Firm*—Ratner & Prestia

[57] ABSTRACT

In a method and an apparatus for recovering a sterilizing gas, in particular ethylene oxide, materials to be sterilized are sterilized with the sterilizing gas in a sterilizing chamber; the sterilizing gas/air mixture withdrawn from the sterilizing chamber is predried in a precooler; the predried sterilizing gas/air mixture is freed from residual moisture in a drier, the sterilizing gas liquefied in a low-temperature condenser and stored in a storage container until reuse in the sterilizing chamber. The sterilizing and the entire recovery of the sterilizing gas takes place at pressures beneath the atmospheric pressure surrounding the apparatus.

11 Claims, 2 Drawing Sheets

METHOD AND APPARATUS FOR RECOVERING A STERILIZING GAS

This application is a continuation of application Ser. No. 07/882,486 filed May 13, 1992 now abandoned.

BACKGROUND OF THE INVENTION

1. Field of the Invention

The invention relates to a method and an apparatus for recovering a sterilizing gas, in particular ethylene oxide.

2. Description of the Prior Art

For sterilizing medical equipment, including packaged equipment, it is usual to expose the materials to be sterilized in a sterilizing chamber to a sterilizing gas, usually an alkylene oxide. The ethylene oxide generally employed is a very toxic gas which in combination with air is readily inflammable and explosive, with a lower explosion limit of 2.6% and an upper explosion limit of 100% ethylene oxide content in an ethylene oxide/air mixture. Thus, even without addition of air pure ethylene oxide (ETO) can explode in the presence of a suitable ignition source. To reduce the risks involved therewith, the established practice is to dilute ETO with a relatively inert gas. Typical is a mixture of 12% by weight ETO with 88% by weight Freon R 12 (dichlorodifluoromethane).

To avoid having to release the toxically acting and relatively expensive constituents of such a mixture into the environment after each sterilizing cycle, in recent years methods and apparatuses have been developed for recovering the sterilizing gas and the inert additive gases mentioned. Thus, U.S. Pat. No. 3,549,312 discloses a method and an apparatus for recovering alkylene oxide and the admixed inert constituents in which the mixture of alkylene oxide and the inert additives extracted from the sterilizing chamber by suction is supplied to a precooler and thereafter to an adsorber. The mixture freed from moisture in the adsorber then passes to a condenser for liquefying the alkylene oxide and the admixed Freon R 12 and finally to a reservoir for intermediate storage of the liquid mixture. Finally, this mixture can be supplied to the sterilizing chamber again from the reservoir subjected to excess pressure. Although this publication does refer to the use of pure ethylene oxide as sterilizing gas, a method or an apparatus operating according to this teaching will no doubt be limited to the use of a mixture of ethylene oxide and a relatively inert gas because no steps are apparent for countering the problems of the easy inflammability of pure ethylene oxide and avoiding excess pressure in the sterilizing chamber and the following recovery. Excess pressure can however lead to the escape of toxic gases to the environment.

Further methods and apparatuses for recovering a sterilizing gas or a mixture of a sterilizing gas and usually a gaseous fluorinated hydrocarbon are known from EP-A-0 130 319, U.S. Pat. No. 3,989,461 and EP-A-0 326 985. All the methods and apparatuses disclosed therein operate at least at times and in some areas of such apparatuses at pressures above the ambient pressure, thereby resulting in a continuous danger of leakage losses. Although the possibility of using pure ethylene oxide as sterilizing gas is mentioned in EP-A-0 130 319, the particular problems in the handling thereof and in particular their technical solution are not mentioned. They were obviously not recognized.

SUMMARY OF THE INVENTION

The object of the present invention is therefore to avoid the disadvantages of the methods and apparatuses known from the prior art for recovering sterilizing gases. In particular, such a method and apparatus is to permit more reliable operation with pure ethylene oxide as sterilizing gas.

The invention therefore proposes in a method for recovering a sterilizing gas, in particular ethylene oxide, wherein materials to be sterilized are sterilized in a sterilizing chamber with the sterilizing gas, the sterilizing gas/air mixture extracted from the sterilizing chamber by suction is predried in a precooler, the predried sterilizing gas/air mixture is freed from residual moisture in a drier and the sterilizing gas is liquefied in a low-temperature condenser and stored in a storage container until reuse, the improvement in which the sterilizing and the entire recovery of the sterilizing gas takes place at pressures beneath the atmospheric pressure surrounding the apparatus.

The invention also proposes in an apparatus for recovering a sterilizing gas, in particular ethylene oxide, comprising a sterilizing chamber for receiving the materials to be sterilized, a precooler for predrying the sterilizing gas/air mixture from the sterilizing chamber, a drier for freeing the sterilizing gas/air mixture from residual moisture, a low-temperature condenser for liquefying the sterilizing gas and a storage container for storing the liquefied sterilizing gas, having a return for the sterilizing gas from the storage container to the sterilizing chamber, the improvement of a vacuum pump for maintaining a partial vacuum in the recovery apparatus.

By dispensing with the chlorinated fluorohydrocarbons, for example Freon, usually admixed with a sterilizing gas, firstly a contribution is made to reducing the damage of the ozone layer by chlorinated fluorohydrocarbons escaping into the environment.

The use of a pure sterilizing gas, in particular pure ethylene oxide (ETO), permits a great reduction of the residence time of the materials to be sterilized in a sterilizing chamber because the concentration of the sterilizing gas in the sterilizing gas-air mixture of the sterilizing chamber is now of course higher than when using the aforementioned additives.

Furthermore, a sterilizing chamber operated under a partial vacuum or reduced pressure can be evacuated quicker than the sterilizing chambers known in the prior art and operated at excess pressure, thereby further reducing the residence time of the materials to be sterilized in such a chamber and increasing the degree of utilization of the sterilizing chamber. Since the entire method and the entire apparatus for recovering the sterilizing gas operates at pressures which lie below the ambient pressure, the operating safety is increased as regards the risk of escape of sterilizing gas. Thus, any leaks within an apparatus according to the invention lead only to an influx of air but not to ETO escape into the atmosphere.

It is precisely the use of pure ETO as sterilizing gas which causes particular problems due to its easy inflammability and explosiveness. To enable ETO, preferred as sterilizing gas, to be used (and below reference will be made only to ETO as a representative), the ETO/air mixture withdrawn from the sterilizing chamber is supplied via precooler to a drier and in the latter further freed from residual moisture still present in the mixture by adsorption in a coolable molecular sieve. The adsorption of water vapour in the molecular sieve is exothermic. Furthermore, some ETO is likewise exothermically coadsorbed. This coadsorption rapidly increases with increasing temperature so that when using pure ETO the temperature can quickly rise to the explosion limit. When using the usual mixture of 12% ETO and 88% Freon R 12 the cooling action of the Freon prevents the rise of the temperature in such a molecular sieve. Now, with pure ETO a dangerous temperature rise up to the explosion limit of pure ETO must however be expected. Whereas on a possible explosion propagation in the flow direction, i.e. in the direction towards the section of the apparatus serving for the liquefication of the ETO, can be excluded because of the very low temperatures prevailing there, there is serious possibility of propagation of any explosion back in the direction towards the sterilizing chamber ("blowback"). To prevent such a backflash or blowback, according to the invention the molecular sieve is cooled during the operation, i.e. in the adsorption phase, to suppress from the start any inadmissible temperature rise in the molecular sieve and limit the coadsorption of ETO to the smallest possible value.

Furthermore, in a particularly advantageous embodiment of the invention an effective barrier is provided against the propagation of any explosion and the consequent decomposition reactions of ETO from the molecular sieve in the direction towards the sterilizing chamber. Preferably, a precooler arranged between the sterilizing chamber and molecular sieve represents such a barrier. According to the invention, for this purpose the tubes conducting the ETO/air mixture within the precooler are dimensioned accordingly by mutual adaptation of flow cross-section and flow length.

BRIEF DESCRIPTION OF THE DRAWINGS

The invention will be described in more detail hereinafter with reference to a preferred embodiment with the aid of the drawings. Further advantages and features of the present invention will be apparent. In the drawings.

DESCRIPTION OF THE PREFERRED EMBODIMENT

Figure 1:
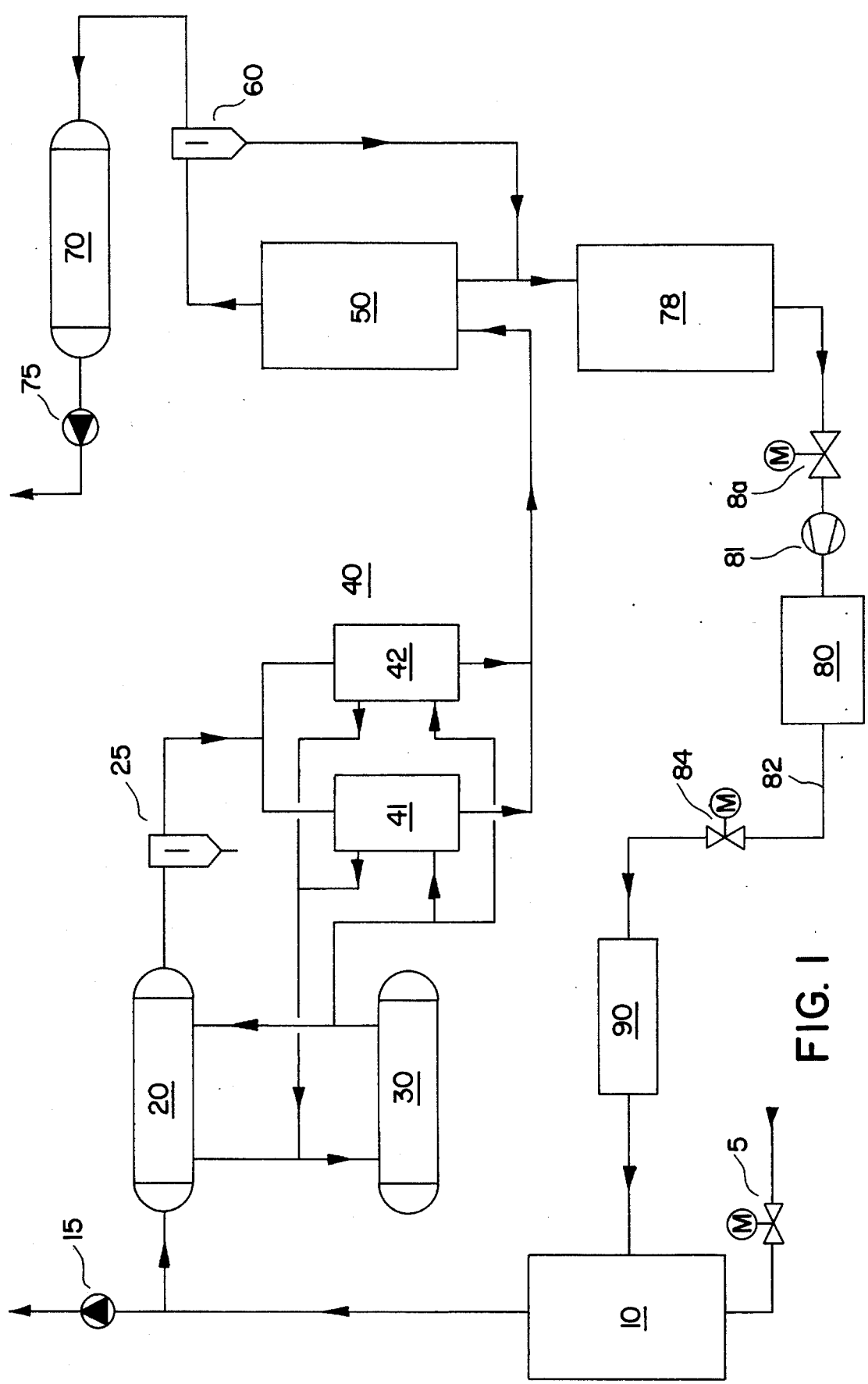
FIG. 1 shows a schematic illustration of a recovery apparatus.

At the start of a sterilizing cycle moist ambient air is allowed into a sterilizing chamber 10 via a closable valve 5 in order to permit initially growth of germs to be killed in the following sterilizing process. After a defined starting state in the sterilizing chamber 10 necessary for the sterilization has been reached in this manner, the sterilizing chamber 10 is first evacuated by a pump 15 down to about 100 mbar before via the heater or evaporator 90 sterilizing gas is conducted into the sterilizing chamber 10 until an absolute pressure therein of about 800 mbar is reached. The chamber pressure thus remains appreciably beneath the pressure of the ambient atmosphere. Following the sterilization the sterilizing chamber 10 is emptied via a vacuum pump 75. The withdrawn sterilizing gas/air mixture—hereinafter as a representative reference will be made only to ethylene oxide (ETO) as sterilizing gas—firstly passes through a precooler 20 in which it is cooled to about 4° to 10° C. In the precooler 20 the major part of the water vapour contained in the ETO/air mixture is liquefied and separated in a following water separator 25. The refrigeration for precooling is made available by an evaporator 30 of a refrigeration machine via a water or brine circuit. The ETO/air mixture now flows to a drier 40 which in the embodiment illustrated is made as moisture-adsorbing molecular sieve 41 or 42. Such a drier 40 comprises two alternately operable molecular sieves 41 and 42. The adsorption phase of the one molecular sieve is used as regeneration phase of the respective other molecular sieve. In the adsorbing molecular sieve 41 or 42 the moisture still contained in the already predried ETO/air mixture is adsorbed to such an extent that the dew point of the ETO/air mixture leaving the drier 40 lies in the range between −80° C. and −100° C. Like the precooler 20, the particular molecular sieve 41 or 42 which is active is cooled by the evaporator 30 of the refrigeration machine.

The ETO/air mixture largely freed from moisture now passes from the drier 40 into a low-temperature condenser 50 which is operated with liquid nitrogen or another suitable refrigerant and in which the ETO/air mixture is reduced to a temperature in the range from −80° C. and −130° C. to liquefy the ETO. The ETO liquefied except for very minute traces passes from the low-temperature condenser 50 either directly or via a condensate separator 60 following the low-temperature condenser 50 to an ETO receiver 78. From there the liquefied ETO is conveyed by a pump 81 to the storage container 80. During the sterilizing and recovery the entire system is subjected to reduced pressure apart from the storage container 80 between the motor valves 8a and 84.

The uncondensable constituents of the ETO-air mixture, substantially air, are withdrawn from the low-temperature condenser 50 via a preheater 70 by the vacuum pump 75 and released to the environment. In the next sterilizing circuit the liquefied ETO then passes from the storage container 80 via a conduit 82 and the closable valve 84 to the ETO evaporator 90 and from there finally in gaseous form to the sterilizing chamber 10.

As trial runs of such an apparatus have shown, when operating with pure ETO as sterilizing gas inadmissibly high temperatures occur in the molecular sieves 41 or 42. The overheating of the molecular sieves 41 or 42 is prevented by active cooling of the adsorption region of such a sieve.

Figures 2, 3:
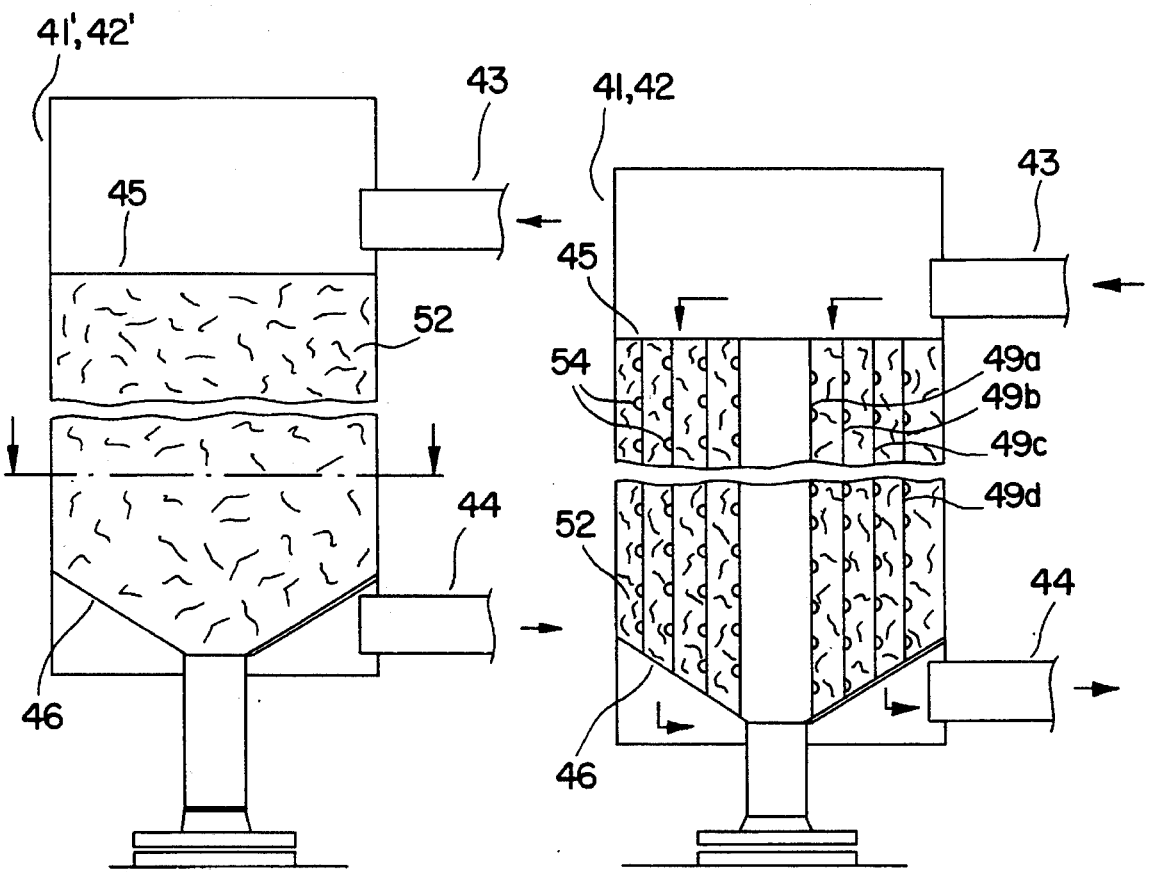
FIG. 2 is an illustration of a conventional molecular sieve in longitudinal section.
FIG. 3 is an illustration of a cooled molecular sieve in longitudinal section.
Figure 4:
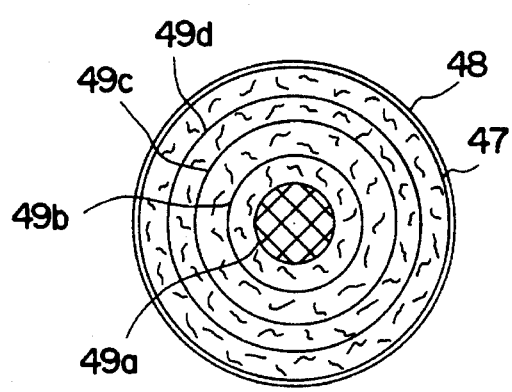
FIG. 4 shows the molecular sieve of FIG. 3 in cross-section.

In FIG. 2 a conventional molecular sieve 41' or 42' is shown in section. This construction suffices for apparatuses in which for sterilization a mixture of 12% ETO and 88% Freon R 12 is used. The gas mixture to be dried is supplied to the molecular sieve 41' or 42' of circular cross-section illustrated by way of example via an upper lateral connection tube piece 43 and withdrawn via a lower lateral connection tube piece 44. In the molecular sieve 41' or 42' the gas mixture flows through the adsorption region 52 which is disposed between an upper and lower sieve 45, 46 and filled with a suitable adsorbent and in which the moisture contained in the gas mixture is adsorbed. When using a mixture of for example ETO and Freon R 12 in the ratio 12:88 the good cooling effect of the Freon R 12 prevents an inadmissible rise of the temperature in the molecular sieve 41' or 42'. Now, to prevent the dangerous temperature rise to be observed when using pure ETO during the moisture adsorption, said rise being up to the explosion limit of the ETO, the adsorption region 52 of the molecular sieve 41 as well as 42 is subdivided into four coolable annular chambers as illustrated in FIGS. 3 and 4. The division into four parts and the annular configuration are however not obligatory choices. Within the outer ring 47, to which for regenerating the molecular sieve 41 or 42 a heating band 48 may be attached to heat the charged adsorbent for the purpose of desorbing, tubes 49a to 49d aligned coaxially and concentrically to each other are arranged. In this specific example of embodiment four tubes 49a to 49d are present, the inner region of the inner tube 49a itself not forming an adsorption region. As is shown in FIG. 3, each of said tubes 49a to 49d is surrounded by a helical cooling conduit 54 welded onto a respective tube. As apparent from FIG. 1, the cooling conduits 54 and thus the molecular sieves 41, 42 are traversed by the water or brine circuit of the refrigeration machine 30. In the example of embodiment illustrated the tubes 49a to 49d, for a diameter of the molecular sieve of about 325 mm, have diameters in rising order of 89, 140, 210 and 280 mm. In this dimensioning example, for instance from the outer annular adsorption region, i.e. from the region lying outside the tube 49d, about 34% of the total thermal power to be dissipated can be taken.

To prevent the propagation of any decomposition reactions of the ETO originating from the molecular sieve 41 and 42 towards the sterilizing chamber 10 a flame barrier is provided between the drier 40 and the sterilizing chamber 10. Propagation of such ETO decomposition reactions to the low-temperature condenser 50 is not to be expected due to the very low temperatures prevailing in the latter. The precooler 20 is configured as flame barrier by appropriate dimensioning of the tubes conducting the ETO/air mixture. The tubes should have a flow cross-section of at the most 18 mm diameter and when such a diameter is chosen a flow length of at least 2 m. Smaller diameters and longer lengths will of course increase the flame-blocking effect.

We claim:

1. A method of recovering ethylene oxide mixture after effecting sterilization of materials in a sterilizing chamber comprising the steps of:

withdrawing ethylene oxide mixed with air, water vapor, and other constituents from said chamber;

pre-cooling said ethylene oxide mixture to a temperature of between 4° C. and 10° C.;

separating a majority of water vapor contained in said pre-cooled ethylene oxide mixture to form a partially dewatered mixture;

passing said partially dewatered mixture through a drier containing a cooled bed of molecular sieve material to further recover water so that a drier effluent mixture having a dew point of between −80° C. and −100° C. is created;

passing said drier effluent to a condenser cooled by a liquified cryogenic refrigerant to liquify said ethylene oxide; and conveying said liquified ethylene oxide to a storage container for reuse as a sterilizing agent.

2. A method according to claim 1 wherein said condenser is cooled by liquid nitrogen to a temperature between −80° C. and −130° C.

3. An apparatus for recovering ethylene oxide from a mixture containing ethylene oxide, air, water vapor and other components comprising in combination:

means to withdraw said mixture from a sterilizing chamber and direct said mixture to a pre-cooler;

a pre-cooler adapted to cool said mixture to a temperature of between 4° C. and 10° C.;

means to remove water vapor condensed in said pre-cooler;

means to conduct said pre-cooled mixture after water separation to a cooled bed of moisture absorbing molecular sieve adapted to produce an effluent mixture having a dew point of between −80° C. and 100° C.;

a condenser to condense out ethylene oxide from said mixture; and means to conduct said condensed ethylene oxide to a storage receptacle.

4. An apparatus according to claim 3 wherein the molecular sieve bed has a chamber-like subdivision, at least one respective wall of such a chamber being coolable.

5. An apparatus according to claim 4, wherein the chambers of the molecular sieve are formed by annular chambers concentric with each other, at least one of said annular chamber walls having helically arranged cooling passages.

6. An apparatus according to claim 5, wherein the molecular sieve bed comprises four coolable adsorption chambers.

7. An apparatus according to claim 3, wherein the precooler is arranged between the sterilizing chamber and the drier is constructed as a flame barrier for the sterilizing gas/air mixture.

8. An apparatus according to claim 7, wherein the precooler has tubes traversed by the sterilizing gas/air mixture which are constructed as flame barriers by mutual adaptation of flow length and flow cross-section of said tubes.

9. An apparatus according to claim 8, wherein the tubes of the precooler have a ratio of flow length to flow cross-section of at least 110.

10. An apparatus according to claim 3 wherein there are at least two beds of moisture absorbing molecular sieve so that while one bed is absorbing moisture the other bed can be regenerated.

11. An apparatus according to claim 3 wherein said means for withdrawing said mixture comprises a vacuum pump.

* * * * *